US007105573B2

(12) United States Patent
Krajcik et al.

(10) Patent No.: US 7,105,573 B2
(45) Date of Patent: Sep. 12, 2006

(54) METHODS AND COMPOSITIONS FOR THE TREATMENT OF ALOPECIA AND OTHER DISORDERS OF THE PILOSEBACEOUS APPARATUS

(75) Inventors: Rozlyn A. Krajcik, Poughquag, NY (US); Norman Orentreich, New York, NY (US)

(73) Assignee: Orentreich Foundation for the Advancement of Science, Inc., New York, NY (US)

( * ) Notice: Subject to any disclaimer, the term of this patent is extended or adjusted under 35 U.S.C. 154(b) by 32 days.

(21) Appl. No.: 10/073,607

(22) Filed: Feb. 11, 2002

(65) Prior Publication Data

US 2002/0143039 A1    Oct. 3, 2002

Related U.S. Application Data

(63) Continuation of application No. PCT/US01/05653, filed on Feb. 23, 2001.

(60) Provisional application No. 60/184,398, filed on Feb. 23, 2000.

(51) Int. Cl.
*A61K 31/155* (2006.01)

(52) U.S. Cl. .................................. 514/635

(58) Field of Classification Search ................. 514/635
See application file for complete search history.

(56) References Cited

U.S. PATENT DOCUMENTS

| 4,684,635 | A | | 8/1987 | Orentreich et al. |
| 5,043,162 | A | | 8/1991 | Trager |
| 5,091,596 | A | | 2/1992 | Kennington et al. |
| 5,124,360 | A | | 6/1992 | Larner et al. |
| 5,292,747 | A | | 3/1994 | Davis et al. |
| 5,407,944 | A | | 4/1995 | Goldman |
| 5,550,166 | A | | 8/1996 | Ostlund et al. |
| 5,594,015 | A | | 1/1997 | Kurtz et al. |
| 5,721,230 | A | | 2/1998 | Harris et al. |
| 5,827,896 | A | | 10/1998 | Ostlund et al. |
| 6,075,005 | A | * | 6/2000 | Lurie ........................ 514/2 |

FOREIGN PATENT DOCUMENTS

| FR | 3.203 M | | 1/1964 |
| FR | 2 320 735 A | | 3/1977 |
| GB | 1401518 | * | 7/1975 |
| WO | WO 97 00076 A | | 1/1977 |
| WO | WO 95/05146 A1 | | 2/1995 |

OTHER PUBLICATIONS

Califano et al. "Experience with the topical application of spironolactone as an antiandrogen for the treatment of acne." Clin Ter, 1990 135 (3), pp. 193-199.*
Databast in ACS Imsproduct AN 94:25203, Drug Launches, (Jun. 6, 1988).*
Bronaugh, R.L. et al., "Methods for in vitro percutaneous absorption studies IV: The flow-through diffusion cell," J. Pharm. Sci., 74(1):64-7 (Jan. 1985) (abstract only).
Chukwumerije, O. et al., "Studies on the Efficacy of Methyl Esters of n-Alkyl Fatty Acids as Penetration Enhancers," The J. Invest. Dermatol. 93:349-352 (1989).
DeFronzo, R.A., "Pharmacologic Therapy for Type 2 Diabetes Mellitus," Annals of Internal Medicine, 131(4):281-303 (Aug. 17, 1999).
Delgado-Charro, M.B., et al., "Percutaneous Penetration and Transdermal Drug Delivery," Progress in Dermatology (Publ. of Dermatology Foundation, Evanston, IL), 32(4):1-12 (Dec. 1998).
Drug News & Perspectives, The Year's New Drugs Sections, The Year's New Drugs, 1997, 11(1):15 (Jan. 19, 1998).
Dunaif, A, et al., "The insulin-sensitizing agent troglitazone improves metabolic and reproductive abnormalities in the polycystic syndrome," J. Clin. Endocrinol Metab (United States), 81(9):3299-3306 (Sep. 1996) (abstract only).
Edelman, S.V., "Troglitazone: A New and Unique Oral Anti-Diabetic Agent for the Treatment of Type II Diabetes and the Insulin Resistance Syndrome," Clinical Diabetes, 60-65 (Mar./Apr. 1997).
Lohray, B.B., et al., "Novel Euglycemic and Hypolipidemic Agents," J. Med. Chem., 41:1619-1630 (1998).
Nemecz, G., "Saw Palmetto," U.S. Pharmacist, pp. 97-102 (Jan. 1998).
Osborne, D.W., et al., "Skin Penetration Enhancers Cited in the Technical Literature," Pharmaceutical Technology Articles, 21(11):58 (Nov. 1997).
Price, V.H., "Drug Therapy—Treatment of Hair Loss," The New England Journal of Medicine, 341(13):964-973 (Sep. 23, 1999).
Rezulin™ Product Insert, Parke-Davis, 8 pages, Morris Plains, New Jersey, U.S.A. (Jan. 1997).
Rezulin™ Product Insert, Parke-Davis, Morris Plains, New Jersey, U.S.A. (May 1997).
Sawaya, M.E., et al., "Androgenetic Alopecia—New Approved and Unapproved Treatments," Dermatologic Clinics—New and Emerging Therapies, 18(1):47-61 (Jan. 2000).
Sinclair, R., "Diffuse hair loss," International Journal of Dermatology, 38(1):8-18 (1999).
Ünlühizarci, K., et al., "The effects of metformin on insulin resistance and ovarian steroidogenesis in women with polycystic ovary syndrome," Clinical Endocrinology, 51:231-236 (1999).
Waterworth, D.M. et al., "Linkage and association of insulin gene VNTR regulatory polymorphism with polycystic ovary syndrome," The Lancet, 349(9057:986-990 (Apr. 5, 1997) (abstract only).
White, Jr., J.R., et al., "Insulin Sensitizers—New Options for Treating Type 2 Diabetes," U.S. Pharmacists, pp. 124-243 (Nov. 1999).

* cited by examiner

*Primary Examiner*—Sreeni Padmanabhan
*Assistant Examiner*—Jennifer Kim
(74) *Attorney, Agent, or Firm*—Akin Gump Strauss Hauer & Feld, LLP

(57) ABSTRACT

Insulin sensitivity increasing substances (ISIS), including but not limited to D-chiro-inositol, thiazolidinedione and derivatives, and biguanides, are useful in the treatment of hair loss and other disorders of the pilosebaceous apparatus (hirsutism, acne, etc.) associated with conditions of excess insulin and/or insulin resistance. The treatment comprises administering to a mammal, such as a human, at least one ISIS either alone or in combination with at least one agent, such as an androgen receptor blocker (ARB) and/or a steroid enzyme inhibitor or inducer (STI). Additionally, an activity enhancing agent may be included for topical administration.

14 Claims, No Drawings

METHODS AND COMPOSITIONS FOR THE TREATMENT OF ALOPECIA AND OTHER DISORDERS OF THE PILOSEBACEOUS APPARATUS

CROSS-REFERENCE TO RELATED APPLICATIONS

This application is a continuation of International Application No. PCT/US01/05653, filed Feb. 23, 2001 and published in the English language on Aug. 30, 2001 under International Publication No. WO 01/62237, the disclosure of which is incorporated herein by reference, which itself claims priority under 35 U.S.C. § 119(e) to prior U.S. Provisional Patent Application No. 60/184,398, filed Feb.23, 2000.

BACKGROUND OF THE INVENTION

Hair loss and other disorders of the mammalian pilosebaceous apparatus (hair/oil gland) remain a great source of distress and concern today for many afflicted patients. There have been suggestions in the literature that severe male pattern baldness (occurring before the age of thirty) is the male phenotype of the polycystic ovarian syndrome (PCOS), a common endocrine abnormality in women that leads to infertility and obesity (although some PCOS patients are lean). Another feature of PCOS is profound insulin resistance which occurs in both obese and lean patients. This excess insulin in PCOS is believed to drive excess androgen production which results in hyperandrogenism in some PCOS patients. It has been assumed that it is the hyperandrogenism that causes the diffuse hair loss and hirsutism noted in a subset of these women.

Male pattern baldness, also called andro(chrono)genetic alopecia, has long been recognized as the result of androgens acting over time on genetically susceptible hair follicles. However, it is becoming evident that mechanisms other than those which implicate androgen activity are involved in hair loss disorders. In fact, many female hair loss sufferers do not have elevated male hormones, and local or systemic treatment with androgen receptor blocking agents or steroid enzyme inhibitors does not restore hair growth. Nor are these agents overwhelmingly successful in treating balding males, suggesting that some other mechanism is contributing to the balding process.

Since the physiological mechanisms contributing to hair loss and other disorders of the pilosebaceous apparatus in mammals, such as humans, are only partially understood, there is an unmet need in the art for compositions and methods useful in the treatment of hair loss and other disorders of the pilosebaceous apparatus.

BRIEF SUMMARY OF THE INVENTION

The present invention provides a method for treating a disorder of the pilosebaceous apparatus (hair/oil gland) of a mammal. As used herein, the term "treatment" or "to treat" includes inhibiting, reducing, or reversing the loss of hair in a mammal, or alleviating any symptom of a disorder of the pilosebaceous apparatus of a mammal. The method comprises administering to a mammal, such as a human, an insulin sensitivity increasing substance (ISIS) in an amount effective to treat a disorder of the pilosebaceous apparatus of the mammal, in a manner so as to reach the affected area of the pilosebaceous apparatus. The ISIS is any substance capable of increasing the physiological sensitivity of a mammal to any one or more of the biological actions of insulin. The ISIS can be, by way of example and not by limitation, a drug, a sugar or carbohydrate, a peptide or a protein. The ISIS can be administered by any known route of administration, for example by topical or oral administration or by injection. The ISIS can be provided either directly, by contacting it with the affected area, or indirectly through the action of any biological process. The disorder treated may be, for example, alopecia (hair loss disorders) of any type or origin, acne, hirsutism, or superfluous hair growth.

In one embodiment, the ISIS is a member of a class of compounds termed thiazolidinediones, including derivatives thereof.

In another embodiment, the ISIS is a member of a class of compounds termed biguanides, including derivatives thereof.

In a further embodiment, the ISIS is D-chiro-inositol, including derivatives thereof.

In one aspect, the method of the invention further comprises administering to the mammal at least one of an androgen receptor blocking agent (ARB) and a steroid enzyme inhibitor or inducer (STI). When present, the ARB is administered in an amount effective to block androgen receptor activity in a mammal. The STI, when present, is administered in an amount effective to inhibit or induce the activity of a steroid enzyme in a mammal.

In another aspect, the method of the invention comprises administering to the mammal an activity enhancing agent where any ISIS alone or in combination with an ARB and/or STI is administered topically. The activity enhancing agent is administered in an amount effective to enhance the activity of either the ISIS alone, or in combination with an ARB and/or STI when administered topically in a method of treating a disorder of the pilosebaceous apparatus of the mammal. The activity enhancing agent can be any substance or combination of substances capable of achieving this effect. Preferably, the activity enhancing agent comprises at least one substance selected from the group consisting of a penetration-enhancing agent, a vasodilator, an anti-inflammatory agent, a glucose/insulin regulator, a glycosylation inhibitor, and an endogenous or exogenous effector.

The invention also includes compositions for treating a disorder of the pilosebaceous apparatus of a mammal. The compositions comprise an ISIS in an amount effective to treat a disorder of the pilosebaceous apparatus of a mammal, and optionally at least one ARB, STI and/or activity enhancing agent, as defined above.

DETAILED DESCRIPTION OF THE INVENTION

The present invention relates to methods and compositions for treating a disorder of the pilosebaceous apparatus (hair/oil gland) of a mammal. Such disorders include, by way of example and not by limitation, alopecia (hair loss disorders), acne, hirsutism, and superfluous hair growth. The alopecia can be of any type or origin, including, for example, autoimmune, androgenic, senile, scarring, diffuse, pattern, partial or total alopecia. The mechanism of loss of hair in the mammal to be treated can be either androgen dependent or non-androgen dependent.

In its broadest aspects, the methods and compositions of the present invention are based on the use of an insulin sensitivity increasing substance (ISIS) which is effective against any one or more of the causes of insulin resistance.

A defect in any one or more of several molecular mechanisms can lead to diminished physiological sensitivity of a mammal to one or more of the biological actions of insulin (i.e., insulin resistance). For example, a classical, but not common, defect (genetic mutation) occurs in the insulin receptor itself, which either reduces its ability to bind insulin or its ability to phosphorylate tyrosine residues. More common causes of insulin resistance include down regulation of the number of insulin receptors due to high levels of circulating insulin or functional inactivation of receptors due to anti-insulin receptor antibodies in patients who are susceptible to autoimmune diseases. The causes of the majority of cases of insulin resistance are, however, simply not known at this time, but are suspected to be due to any number of defects in the myriad of signaling molecules downstream of the insulin receptor. Therefore, the potential mechanisms of action of any one particular ISIS can also be broad and numerous.

Insulin resistance could also be the result of defective pancreatic beta cells which may over-produce or hypersecrete insulin in response to normal blood glucose levels. Compensatory mechanisms in skeletal muscle, adipose tissue, and liver can then occur which down regulate the ability of those tissues to respond to elevated insulin.

Insulin resistance can also result from excess weight gain, particularly abdominal fat mass accretion which leads to high levels of fatty acids in the portal circulation. The effect of excess fatty acids on the liver is interference with insulin stimulated glucose metabolism and subsequently, insulin resistance. Over-production of tumor necrosis factor alpha (TNF-alpha) and other products by fat cells (adipocytes) can also interfere with insulin action.

Insulin resistance can also result from high dietary intake of sucrose and/or fructose especially in the form of highly processed foods containing high fructose corn syrup which can lead to high triglyceride and free fatty acid levels. Also, diets deficient in such supplements as magnesium, copper, chromium, vanadium, and others can lead to insulin resistance. Additionally, metabolic acidosis can reduce the effectiveness of insulin.

Therefore, drugs or compounds which normalize pancreatic beta cells or stabilize/reduce fat stores (anti-obesity drugs), alter dietary intake of sucrose/fructose, agents that adjust blood pH or block the production or action of cytokines, such as TNF-alpha, or metabolic products, such as free fatty acids, could all potentially decrease insulin resistance in addition to the ISIS mechanisms outlined above.

In one embodiment, the ISIS is a member of the class of compounds termed thiazolidinediones, including derivatives thereof. Examples of such compounds include, troglitazone, ciglitazone, pioglitazone, rosiglitazone, and englitazone. The thiazolidinediones are known compounds and are described for example in B. B. Lohray et al., "Novel Euglycemic and Hypolipidemic Agents," *J. Med. Chem.*, 41:1619–1630 (1998) including bibliography thereof; S. V. Edelmann, M.D., "Troglitazone: A New and Unique Oral Anti-Diabetic Agent for the Treatment of Type II Diabetes and the Insulin Resistance Syndrome," *Clinical Diabetes*, pp. 60–65 (March/April 1997); U.S. Pat. No. 5,594,015 of Kurtz et al.; and J. R. White et al., "Insulin Sensitizers," *US Pharmacist*, pp. 124–132 (Nov. 1999).

In another embodiment, the ISIS is a member of a class of compounds termed biguanides, including derivatives thereof. The biguanide can be either synthetic (including alkyl or aromatic compounds) or natural. Biguanides and derivatives thereof are known compounds and are described, for example, in S. Shapiro et al., *J. Amer. Chem. Soc.*, 81(14): 3728–3736 (1959). Preferably, the biguanide is metformin hydrochloride, available, for example, as Glucophage® metformin hydrochloride tablets from Bristol-Myers Squibb Co., Princeton, N.J.

In another embodiment, the ISIS is D-chiro-inositol, including derivatives thereof. This compound is a known compound and is described, for example in U.S. Pat. Nos. 5,124,360 and 5,091,596; and R. E. Ostland, Jr., "D-Chiro-Inositol and Insulin Action." Chiro-inositols are available commercially from Industrial Research Limited (New Zealand).

In the methods of the invention, the ISIS can also be administered in the form of various pharmaceutical compositions comprising an ISIS, discussed herein below, for example.

The ISIS can be administered by any method of administering a compound or a pharmaceutical composition to a mammal. Such methods are known to the skilled artisan, and include, by way of example and not by limitation, oral administration (either locally or enterally), administration by injection (either locally or systemically), topical administration (either locally or transdermally), and transmucosal administration.

The invention also includes compositions for treating a disorder of the pilosebaceous apparatus of a mammal (e.g., a human). Such disorders include any of the disorders described herein. These compositions can be, by way of example and not by limitation, in the form of a cream, a shampoo, a tincture, a gel, an ointment, or a patch for topical administration; a pill, tablet or solution for oral administration; a sterile solution for injection; or a pellet for implantation. The inventive compositions are useful for treating any of the disorders discussed above in an affected mammal. As discussed above, the mammal may be any mammal, but is preferably a human.

In the inventive compositions and methods, the ISIS is administered in an amount effective to treat a disorder of the pilosebaceous apparatus of a mammal. The ISIS can be provided either directly, by contacting it with the affected area, or indirectly through the action of any biological process. This amount will vary depending upon the particular ISIS used, the route of administration selected, the type of disorder being treated, the species, age, weight and sex of the treated mammal, and possibly other factors.

Examples of dosages for certain ISIS compounds are set forth below. As used herein, unless otherwise indicated, all percentages are percent by weight of the total composition.

| Primary ISIS compounds | | Oral (daily) | Topical (conc.) |
|---|---|---|---|
| Troglitazone: | Preferred | 200–600 mg | 0.01–10% |
| | More Preferred | 400–600 mg | 0.1–2.0% |
| | Most Preferred | 400 mg | 0.5–1.0% |
| Rosiglitazone: | Preferred | 2–16 mg | 0.0001–10% |
| | More Preferred | 4–8 mg | 0.001–2% |
| | Most Preferred | 4 mg | 0.01–1% |
| Pioglitazone: | Preferred | 7.5–60 mg | 0.001–10% |
| | More Preferred | 15–45 mg | 0.01–2% |
| | Most Preferred | 15–30 mg | 0.1–1% |
| Metformin: | Preferred | 250–2550 mg | 0.01–10% |
| | More Preferred | 1000–2000 mg | 0.05–5% |
| | Most Preferred | 1700–2200 mg | 0.08–2% |
| D-Chiro-Inositol: | Preferred | 100 mg–5 gm | 0.01–20% |
| | More Preferred | 1 gm–2 gm | 0.1–10% |
| | Most Preferred | 1200–1600 mg | 0.1–5% |

Topical formulations can be applied once, twice, three, four, or more times a day in a quantity sufficient to cover the affected area.

The various disorders of the pilosebaceous apparatus would not require different dosages or frequency of dosing. The preferred route for metformin and troglitazone is topical, but topical in conjunction with oral may eventually prove to be more effective. The preferred route for D-chiro-inositol is oral.

In another embodiment, the compositions and methods of the invention comprise, in addition to administering an ISIS, administering an androgen receptor blocking agent (ARB) to the mammal in an amount effective to block androgen receptor activity in the mammal and is present in an amount effective to enhance the efficacy of the ISIS. The ARB may be any of the androgen receptor blocking agents described herein. Preferably, the ARB is a compound selected from the group consisting of cyproterone acetate, flutamide, RU-58841, bicalutamide, nilutamide, canrenone, spironolactone, progesterone, 4MA, ketoconazole, cimetidine, and derivatives thereof. The ARB may be administered orally or topically, for example, in dosages known in the art, for example from M. E. Sawaya et al., "Androgenetic Alopecia: New Approved and Unapproved Treatments," *New and Emerging Therapies*, 18(1): 47–61 (2000), again depending upon a number of factors as mentioned above, such as the particular ARB used, administration route, disorder treated, and various characteristics of the mammal treated.

In another embodiment, the compositions and methods of the invention comprise, in addition to administering an ISIS, administering a steroid enzyme inhibitor or inducer (STI) to the mammal in an amount effective to inhibit or induce the activity of a steroid enzyme in the mammal. The STI should preferably enhance the efficacy of the ISIS in treating any of the disorders of the pilosebaceous apparatus described herein. The STI can be a member of any class of compounds effective at inhibiting or inducing a steroid enzyme in a mammal. Preferably, the STI is either a 5-alpha reductase inhibitor (ARI), a 3-alpha hydroxy steroid dehydrogenase inhibitor or a 17-beta hydroxy steroid dehydrogenase inducer. Examples of preferred compounds of these classes include, but are not limited to, finasteride, MK 386, epigallocatechin gallate, beta-sitosterol, saw palmetto, permixon, pygeum africanum, progesterone, 5-alpha dihydroprogesterone, 4 MA, spironolactone, canrenone, FK-143, turosteride, and derivatives thereof. The STI is administered, preferably orally or topically, in an amount known in the art per se. See e.g., Sawaya et al. above; G. Nemecz, "Saw Palmetto," *US Pharmacist*, pages 97–102 (January 1998); U.S. Pat. Nos. 4,684,635 and 5,407,944. Again, the amount will depend upon a number of factors as mentioned above, such as particular STI used, administration route, disorder treated, and various characteristics of the mammal treated.

In a further embodiment, the method of the invention comprises, in addition to administering the ISIS, administering to the mammal both an ARB and an STI. As evident from the above listed examples of ARB and STI, some compounds, such as progesterone, 4MA, spironolactone, and canrenone, function as both an ARB and an STI. When present, the ARB and/or STI compound can be administered by any of the routes of administration discussed herein. Additionally, the ARB and/or STI compound can be administered in either the same or a separate vehicle as the ISIS, or can be administered either prior to, simultaneous with, or after administration of the ISIS to the mammal. The amounts will not differ from the use of ARB or STI alone, as discussed above. These compounds are usually used in long term (chronic or maintenance) therapies. The sequence of application or timing of administration of ARB/STI relative to ISIS is not so important as compliance (i.e., faithful use). The steroidal compounds are usually longer acting than metformin or D-chiro-inositol or even thiazolidinediones. Therefore, once daily dosing of most ARB/STI, in contrast to more frequent (twice or thrice daily) ISIS dosing, may be expected, but this does not add to the inherent synergism of the therapies.

The inventive compositions and methods can, optionally, further comprise administering to the mammal an activity-enhancing agent where any ISIS alone or in combination with an ARB and/or STI is to be administered topically. The activity enhancing agent is administered in an amount effective to enhance the activity of either the ISIS alone, or in combination with an ARB and/or STI when administered topically in a method of treating a disorder of the pilosebaceous apparatus of a mammal. The activity enhancing agent can be any substance or combination of substances capable of achieving this effect.

Preferably, the activity enhancing agent comprises at least one substance selected from the group consisting of a penetration-enhancing agent, a vasodilator compound, an anti-inflammatory agent, a glucose/insulin-regulating compound, and an endogenous or exogenous effector.

Penetration-enhancing agents are known in the art, and include, by way of example and not by limitation, SR-38 (4-decyloxazolidin-2-one), N-methylpyrolidone, DMSO (dimethylsulfoxide), DCMS (decylmethylsulfoxide), glycols, alcohols, fatty acids, esters, surfactants, urea, MAO (myristylamine oxide), Azone®, SEPAL®, vitamin A acids, alpha and beta hydroxy acids, and derivatives thereof. Penetration-enhancing agents are discussed generally in M. Begona Delgado-Charro et al., "Percutaneous Penetration and Transdermal Drug Delivery," *Progress in Dermatology*, 32(4): 1–12 (December 1998) and D. W. Osborne et al., "Skin Penetration Enhancers Cited in the Technical Literature" (1997). The amount of the penetration-enhancing agent in the ISIS formulation may vary widely, depending on the particular agent and use, from a fraction of a percent up to almost 100% where the penetration-enhancing agent also serves as the vehicle or solvent for the ISIS. SR-38, available commercially from Technical and Chemical Products, Inc. (Florida), is a particularly preferred penetration-enhancing agent for use in the present invention and may be present in ISIS formulations at a concentration of about 1–10% of the solution.

Vasodilator compounds are known in the art, and include, by way of example and not by limitation, minoxidil, diazoxide, prazosin, nicotinic acid and its esters, VIP (vasoactive intestinal peptide), maxadilan, nitroglycerin, isosorbide dinitrate, calcium channel blockers, such as nifedipine, and others. The vasodilators may be present in a topical ISIS solution up to several percent by weight depending on the vasodilator used.

The use of anti-inflammatory agents is known to the skilled artisan in dermatological applications. Such compounds include, by way of example and not by limitation, any and all natural or synthetic steroidal and non-steroidal anti-inflammatory compounds, such as cortisone or hydrocortisone.

The glucose/insulin-regulating compound can be any compound capable of regulating glucose and/or insulin metabolism. Examples of such compounds include acarbose and metformin.

An endogenous or exogenous effector is any bodily product or substance made within the patient and having effect within that patient (endogenous) or any manufactured drug or any plant, mineral, or animal derived substance provided to the patient by any route (exogenous) that interacts in a favorable way or promotes or enhances the activity of an ISIS, an AR, or an STI. Such compounds include, by way of example and not by limitation, biotin, DHEA, saw palmetto (permixon), vitamin D substances, folic acid, copper chloride, zinc (also an STI), protein-metal complexes, growth factors, growth hormones, cytokines, and hormones. Amounts of such effectors and additives are known in the art and may be administered as desired.

The inventive compositions can be administered using any of the routes of administration and dosage regimens discussed herein, including, for example, the administration of components of the compositions separately.

Pharmaceutical compositions comprising an ISIS as an active ingredient may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a pharmaceutically acceptable salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "pharmaceutically acceptable salt" means a salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology.

The invention will now be described with reference to the following Examples. These Examples are provided for the purpose of illustration only and the invention should in no way be construed as being limited to these Examples, but rather should be construed to encompass any and all variations which become evident as a result of the teaching provided herein.

EXAMPLE 1

The Effect of a Biguanide ISIS on Hair Loss in Mice

The objective of the experiments in this Example is to examine the effects of the biguanide ISIS metformin on hair loss in aged female obese (C57BL/6J-ob/ob) mice. The hypothesis tested is that metformin, when administered in these mice at a relatively young age, will increase insulin sensitivity, thereby preventing or slowing the progression of hair loss.

Metformin (Glucophage®, Bristol-Myers Squibb Co., Princeton, N.J.) is a biguanide ISIS used clinically for the treatment of type II (non-insulin dependent) diabetes (refer to packaging insert for metformin). The antihyperglycemic effect of metformin has been ascribed to increased peripheral glucose disposal, suppression of glucose production by the liver and a decreased rate of intestinal glucose absorption (Hermann, L. S., *Diabetes Metab.* 5:233–245 (1979)). The plasma insulin level is not increased. In animal studies with the obese (ob/ob -Thieller background) mouse, it has been reported that metformin when administered in the drinking water (240 mg/kg/d for 4 weeks) produced an increase in the concentration of hepatocyte high and low (mainly low) affinity insulin receptors. In these studies, metformin lowered plasma insulin levels but did not alter the hypoglycemic response to exogenous insulin (Lord et al., *Diabetologia* 25:108–113 (1983)).

Treatment Regimen:

Animals: Female C57BL/6J Lep, ob/ob. (homozygous) and C57BL/6J Lep <ob/+> (heterozygous) mice are purchased from the Jackson Laboratory (Bar Harbor, Me.). All animals are housed at a density of 2–3 animals per cage and are maintained on a photoperiod of 12 h light: 12 h dark. Food and water are provided ad libitum.

Test material: Metformin HCL was dissolved in the drinking water at a dosage of 240 mg/kg/d. The dosage is adjusted each week to reflect changes in body weight. Since the animals are group housed, the adjustment is made based on the mean weight of the treatment group, rather than on an animal-to-animal basis. The water is changed twice per week. Periodically the concentration of the metformin in the drinking water is verified by HPLC.

Experimental groups: The ob/+ animals are not entered into the study until two weeks after the ob/ob mice. No ob/+ mice were available at the age group required for these studies {7 weeks}. Thus, once the ob/+ are 7 weeks of age, they are entered in the study.

Parameters monitored: Body weight, food and water consumption are monitored twice per week. Blood samples are collected from the orbital sinus of unanesthesized mice at the baseline and on a monthly basis for the duration of the study. These blood collections are designed to monitor serum glucose and insulin levels. C-peptide and insulin-like growth factor 1 (IGF-1) are also monitored periodically throughout the study. Blood samples for C-peptide analysis are collected following an overnight fast. Selected animals are photographed throughout the study to document the slowing or progression of hair loss.

| Genotype of mice | Number of mice | Treatment |
|---|---|---|
| ob/ob | 11 | Water - Pelleted 5001 Chow |
| ob/ob | 12 | Metformin 240 mg/kg p.o. - Pelleted 5001 Chow |
| ob/+ | 6 | Water - Pelleted 5001 Chow |
| ob/+ | 6 | Metformin 240 mg/kg p.o. - Pelleted 5001 Chow |

The results of this initial study indicate that onset of hair loss in female ob/ob mice is delayed by metformin treatment. Clear differences between control and metformin treated animals were detectable by 10 months of age (corresponding to nearly 8 months of treatment). At that time, hair loss was observed in 36% of the control ob/ob mice, while only 8% of the metformin treated animals were affected. Hair loss was not observed in control or metformin treated ob/+ mice.

EXAMPLE 2

Formulation of Metformin HCl, a Biguanide ISIS

Metformin hydrochloride (HCl) is a white crystalline powder which is highly soluble in water. For production of the test materials described herein, it is dissolved in water to twice the desired final concentration, then mixed with an equal volume of a solution of 4% butylene glycol in special denatured alcohol (SDA) for a final concentration of 50% SDA and 2% butylene glycol. Metformin HCl is soluble in water up to 20% or more, allowing for concentrations of at least 10% by weight. Depending on patient sensitivity to this compound, concentrations of metformin HCl can be reduced as necessary. Preferred concentrations are about 0.8% to about 2.0%.

The pH of this metformin HCl solution is normally 6.5–7.0, but may be adjusted using sodium hydroxide (NaOH) to pH 13 to improve penetration to the dermis. Penetration of metformin HCl improves as pH increases. Any pH between 6.5 and 13.5 is acceptable, but pH values above 7.0 are preferred. If more neutral solutions are required, a penetration enhancing agent should be used to help deliver the drug to the dermis. Several penetration enhancing agents have been tested. Some, like dimethylsulfoxide (DMSO), are applied to the skin for 10–15 minutes prior to administration of the drug, while others, such as myristylamine oxide (MAO), SEPA and N-methyl pyrrolidone (NMP), can be added to the inventive composition in the appropriate concentration before applying to the skin.

Decylmethylsulfoxide (DCMS) is an interesting penetration enhancing agent because it can be applied to the skin as a pre-treatment like DMSO or mixed with the inventive composition. Concentrations as low as 1% promote penetration of up to 20% of the applied metformin dose, while 10% DCMS mixed with metformin allows over 90% of the inventive composition to pass through the dermis.

Metformin base or its HCl or pamoate salts are applied to the skin in a vehicle consisting of 50% SDA and 2% butylene glycol in water. The pH of the base solution is 13, which penetrates the skin readily (75%–88% absorbed after six hours), but causes significant irritation to the skin, including severe burning and redness. The hydrochloride and pamoate salts are at neutral pH, cause no irritation, but fail to penetrate the skin (<1% absorbed in six hours). When combined with penetration enhancers, the percutaneous absorption of metformin increases as shown below:

| Metformin HCl alone | . . . + 0.1% Myristalamine oxide (MAO) | . . . + 7% N-methyl-pyrilodone | . . . + Dimethyl Sulfoxide (DMSO) | . . . + Decamethyl Sulfoxide (DCMS) |
|---|---|---|---|---|
| <1% absorbed | 82% | 24% | 12% | >95% |

| . . . + 10% SEPA | . . . + 0.5% SR-38 | . . . + 1% SR-38 | . . . + 2% SR-38 |
|---|---|---|---|
| 30% | 50% | 63% | 75% |

Penetration of metformin pamoate is similarly improved by the addition of SR-38 to the formula. This compound causes only mild, temporary redness on the skin of the hairless mouse during 11 days of treatment (50 μL, 2× per day).

The HCl can be cleaved from the metformin molecule using NaOH, yielding a basic solution (pH 13.0–13.5), which penetrates the skin better than the hydrochloride. It is important to remove the salts that are produced during this process. Therefore, the mixture is lyophilized, and the dry powder reconstituted in absolute ethanol. The metformin base is somewhat soluble in ethanol, but the salts remain in the solid phase and are left behind when the alcohol/metformin mixture is decanted. This mixture is then dried in a vaccuum oven, and the remaining powder is metformin base. When reconstituted using the procedure above, the solution has a pH of about 13.

A preferred formulation for metformin in water is:

| | |
|---|---|
| Metformin HC1 | 0.8% |
| Butylene glycol | 2.0% |
| SDA alcohol | 50.0% |
| SR-38 (penetration enhancer) | 1.0% |

Primary irritation studies testing this formulation on the skin of female SKH1 hr/hr mice showed essentially no erythema or scaling after 14 days of application (monday-friday; no application on weekends).

EXAMPLE 3

Topical Activity and Formulation of a Biguanide ISIS and its Synthetic or Natural Derivatives Biguanide ($NH_2C({=}NH)NHC({=}NH)NH_2$) and its synthetic derivatives, such as monomethyl, dimethyl, trimethyl, tetramethyl and phenyl compounds are all water soluble, highly alkaline bases with limited long-term chemical stability in water. When neutralized with an appropriate concentration of a strong acid (e.g., HCl, $H_2SO_4$) or a weak organic acid (e.g., glycolic, lactic, citric, pamoic) to about a neutral pH value of approximately 4 to 8, the topical activity of biguanide and its derivatives is maintained, and its chemical stability in water is improved.

When pharmaceutically acceptable salts of biguanide were applied in reasonable concentrations (e.g., about 0.5% to about 10%) in a suitable topical vehicle (e.g., solution, tincture, gel, lotion, cream or ointment) containing a suitable penetration enhancing agent (e.g., surfactant, DMSO, N-methyl pyrrolidone), the growth of hair was stimulated in the obese (ob/ob) mouse model.

Two alopecic female ob/ob mice were treated with 0.8% topical metformin for three months beginning at 13 months of age. Applications of 50 ul were made twice per day (except weekends) to the alopecic (intrascapular) site. After two months of treatment, we detected the presence of pigmentation at the alopecic site (the entire site was not pigmented), which signaled the onset of anagen, the active phase of hair growth. The following week, we observed the presence of small hairs emerging from the skin at these sites. The animals were observed for 6 weeks after the treatment; the new hairs remained intact despite the withdrawal of metformin treatment.

EXAMPLE 4

Typical Topical Preparations of Biguanide (Percentages by Weight)

| Formulation 1: Tincture | |
|---|---|
| Dimethyl biguanide HC1 | 5.0% |
| Myristylamine oxide | 0.1% |
| Water | 6.0% |
| Butylene glycol | 4.0% |
| Denatured alcohol qsad | 100.0% |
| Formulation 2: Gel | |
| Phenyl biguanide | 1.0% |
| Decylmethyl sulfoxide | 5.0% |
| Carbomer | 0.2% |
| Water | 6.0% |
| Butylene glycol | 4.0% |
| Isopropanol qsad | 100.0% |

EXAMPLE 4-continued

Typical Topical Preparations of Biguanide (Percentages by Weight)

Formulation 3: Cream

| | |
|---|---|
| French Lilac Fluid Extract | 30.0% |
| Cholesterol | 3.0% |
| Stearyl alcohol | 3.0% |
| Benzyl alcohol | 4.0% |
| White wax | 8.0% |
| White petrolatum | 52.0% |

EXAMPLE 5

Oral Activity of a Biguanide ISIS in Female Obese Mice

The objective of this second study (compare the initial study of Example 1) was to ascertain whether metformin hydrochloride prevents or slows the progression of age-dependent hair loss in female ob/ob (obese) mice.

Materials and Methods

Twenty-one female C57BL/6J ob/ob mice were purchased from the Jackson Laboratory (Bar Harbour, Me.) at five weeks of age. Following a two-week acclimation time to standard laboratory conditions, the animals were randomly separated into two treatment groups: the control group (received acid water only) and the metformin hydrochloride group (received 240 mg/kg/d of metformin hydrochloride in acid water). Dosages were adjusted on a weekly basis to reflect changes observed in body weight. All animals were group housed and were allowed access to standard laboratory chow and water ad libitum. The progression of hair loss was documented throughout the study.

| Genotype of mice | Number of mice | Treatment |
|---|---|---|
| ob/ob | 11 | Water - Pelleted 5001 Chow |
| ob/ob | 10 | Metformin 240 mg/kg p.o. - Pelleted 5001 Chow |

Results:

The onset of hair loss was delayed by metformin hydrochloride treatment. Clear differences were seen between the incidence of hair loss in control versus metformin hydrochloride-treated animals in animals that were older than 300 days. Excluding animals which exhibited only a possible thinning of the hair coat, the incidence of hair loss in metformin hydrochloride-treated animals at 370 days of age was 30%. In contrast, the controls exhibited a greater than 60% incidence of hair loss. In animals that were 300 days of age, about 20% of the metformin hydrochloride-treated animals exhibited hair loss in contrast to the control animals, which showed about a 40% incidence of hair loss.

Additionally, it was noted in the study that obese mice were prone to a spontaneous skin condition which may resemble human acanthosis nigricans or migratory ichthyosis. Although this condition was not fully characterized, the metformin hydrochloride-treated animal group exhibited markedly less incidence of this skin condition relative to the control animals, the majority of which were affected by the skin condition. In addition, transient changes in hair loss patterns were occasionally noted in some of the animals during the course of the study. For example, an animal which presented with very moderate hair loss (i.e., only possible thinning of hair coat) for a period of two to three weeks might later exhibit no hair loss and sustain that grade for an extended period of time.

EXAMPLE 6

Oral Troglitazone—ob/ob Female Mice Study

This study involved oral administration of troglitazone (Rezulin®) to C57BL/6J Lep (ob) female mice.

Mice:

Non-alopecic female ob/ob mice (7 weeks at start of study) are maintained on a photoperiod of 12 h light:12 h dark. Food (Purina 5001 Meal diet or Purina 5001 with 0.2% troglitazone) and water (acidified pH 2.5) are provided ad libitum.

Test Agent and Experimental Diet:

Troglitazone (Rezulin®) is purchased from Parke-Davis (Morris Plains, NJ) in tablet form. The entire tablet (including the coat) is crushed in a blender prior to being incorporated into the diet. The amount of troglitazone added to the diet is adjusted to account for the weight of the tablet and the actual amount of the drug (400 mg/tablet) incorporated into the tablet.

Evaluation:

The progression of hair loss is monitored by the investigator on a weekly to biweekly basis. The dorsal hair coat is photographed on a monthly basis to chart the onset and/or progression of alopecia.

Result:

At 350 days, 100% of the control animals exhibited some degree of hair loss versus 60% of the mice receiving troglitazone.

It will be appreciated by those skilled in the art that changes could be made to the embodiments described above without departing from the broad inventive concept thereof. It is understood, therefore, that this invention is not limited to the particular embodiments disclosed, but is intended to cover modifications within the spirit and scope of the present invention.

We claim:

1. A method of treating alopecia in a mammal comprising administering to the mammal an insulin sensitivity increasing substance (ISIS) in an amount effective to treat the alopecia in the mammal, in a manner so as to reach an affected area of a pilosebaceous apparatus, wherein the ISIS is a biguanide having a formula $NH_2C(=NH)NHC(=NH)NH_2$, an alkyl or aromatic derivative thereof, or a salt thereof.

2. The method of claim 1, wherein treating alopecia comprises at least one of inhibiting, reducing and reversing the loss of hair in the mammal.

3. The method of claim 1, wherein the ISIS is administered topically to the affected site.

4. The method of claim 1, wherein the ISIS is a biguanide having a formula $NH_2C(=NH)NHC(=NH)NH_2$ and its derivatives selected from the group consisting of monomethyl, dimethyl. trimethyl, tetramethyl and phenyl derivatives, and salts thereof.

5. The method of claim 4, wherein the biguanide is metformin hydrochloride.

6. The method of claim 1, wherein the ISIS is administered orally.

7. The method of claim 1, wherein the mammal is a human.

8. The method of claim 1, further comprising administering to the mammal a steroid enzyme inhibitor or inducer (STI) in an amount effective to inhibit or induce the activity of a steroid enzyme in the mammal.

9. The method of claim 1, wherein the steroid enzyme inhibitor or inducer (STI) is selected from the group consisting of a 5-alpha reductase inhibitor (ARI), a 3-alpha hydroxy steroid dehydrogenase inhibitor, and a 17-beta hydroxy steroid dehydrogenase inducer.

10. The method of claim 1, further comprising administering to the mammal an androgen receptor blocking agent (ARB) in an amount effective to block androgen receptor activity in the mammal.

11. The method of claim 1, wherein the androgen receptor blocking agent ARB is a compound selected from the group consisting of cytoproterone acetate, flutamide, bicalutamide, nilutamide, RU-58841, canrenone, spironolactone, progesterone, 4MA, ketoconazole, and cimetidine.

12. The method of claim 1, further comprising administering to the mammal both an androgen receptor blocking agent (ARB) in an amount effective to block androgen receptor activity, and a steroid enzyme inhibitor or inducer (STI) in an amount effective to inhibit or induce the activity of a steroidal enzyme in the mammal.

13. The method of claim 1, further comprising administering to the mammal an activity-enhancing agent where any ISIS alone or in combination with an androgen receptor blocking agent (ARB) or steroid enzyme inhibitor or inducer (STI) is to be administered topically, wherein the activity-enhancing agent is administered to the mammal in an amount effective to enhance the activity of either the ISIS alone or in combination with the androgen receptor blocking agent (ARB) and/or the steroid enzyme inhibitor or inducer (STI).

14. The method of claim 13, wherein the activity-enhancing agent comprises at least one substance selected from the group consisting of a penetration-enhancing agent, a vasodilator compound, an anti-inflammatory agent, a glucose/insulin regulating compound, and an endogenous or exogenous effector.

* * * * *